US009228178B2

(12) United States Patent
Abbas et al.

(10) Patent No.: US 9,228,178 B2
(45) Date of Patent: Jan. 5, 2016

(54) ENGINEERING OF XYLOSE REDUCTASE AND OVEREXPRESSION OF XYLITOL DEHYDROGENASE AND XYLULOKINASE IMPROVES XYLOSE ALCOHOLIC FERMENTATION IN THE THERMOTOLERANT YEAST *HANSENULA POLYMORPHA*

(75) Inventors: Charles Abbas, Champaign, IL (US); Kostyantyn Dmytruk, Lviv (GB); Olena Dmytruk, Lviv (GB); Andriy Sibirny, Lviv (GB); Andriy Y. Voronovsky, Lviv (GB)

(73) Assignee: Archer Daniels Midland Co., Decatur, IL (US)

( * ) Notice: Subject to any disclaimer, the term of this patent is extended or adjusted under 35 U.S.C. 154(b) by 254 days.

(21) Appl. No.: 12/993,215

(22) PCT Filed: Jun. 1, 2009

(86) PCT No.: PCT/US2009/045813
§ 371 (c)(1),
(2), (4) Date: Nov. 17, 2010

(87) PCT Pub. No.: WO2009/158139
PCT Pub. Date: Dec. 30, 2009

(65) Prior Publication Data
US 2011/0086402 A1 Apr. 14, 2011

Related U.S. Application Data
(60) Provisional application No. 61/057,515, filed on May 30, 2008.

(51) Int. Cl.
C12P 7/06 (2006.01)
C12P 7/10 (2006.01)
C12N 1/19 (2006.01)
C12N 9/12 (2006.01)
C12N 9/04 (2006.01)

(52) U.S. Cl.
CPC ............ *C12N 9/1205* (2013.01); *C12N 9/0006* (2013.01); *C12P 7/06* (2013.01); *C12P 7/10* (2013.01); *C12Y 101/01009* (2013.01); *Y02E 50/16* (2013.01); *Y02E 50/17* (2013.01)

(58) Field of Classification Search
CPC ...... C12N 9/0006; C12N 9/1205; C12P 7/06; C12P 7/18; C12P 7/10; C12Y 207/01017; C12Y 101/01009; C12Y 101/01021
USPC ............... 435/254.2, 255.6, 320.1, 69.1, 190, 435/194; 536/23.2
See application file for complete search history.

(56) References Cited

U.S. PATENT DOCUMENTS

2003/0157675 A1 8/2003 Cordero Otero et al.
2005/0153411 A1 7/2005 Wahlbom et al.
2006/0228789 A1 10/2006 Jeffries et al.
2008/0254524 A1 10/2008 Abbas et al.

FOREIGN PATENT DOCUMENTS

WO WO 97/42307 A1 11/1997

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Bianchi et al., Molecular Biology 19(1):27-38, 1996.*
Ishchuk et al., FEMS Yeast Res 8:1164-1174, available on-line Aug. 22, 2008.*
Zaldivar J, Nielsen J, Olsson L: Fuel ethanol production from lignocellulose: a challenge for metabolic engineering and process integration. Appl Microbiol Biotechnol 2001, 56:17-34.
Chiang C, Knight SC: Metabolism of D-xylose by molds. Nature 1960, 188:79-81.
Eliasson A, Christensson C, Wahlbom CF, Hahn-Hagerdal B: Anaerobic xylose fermentation by recombinant *Saccharomyces cerevisiae* carrying XYL1, XYL2, and XKS1 in mineral medium chemostat cultures. Appl Environ Microbiol 2000, 66:3381-3386.
Tantirungkij M, Nakashima N, Seki T, Yoshida T: Construction of xylose-assimilating *Saccharomyces cerevisiae*. J Ferment Bioeng 1993, 75:83-88.
Toivari MH, Aristidou A, Ruohonen L, Penttila M: Conversion of xylose to ethanol by recombinant *Saccharomyces cerevisiae*: importance of xylulokinase (XKS1) and oxygen availability. Metab Eng 2001, 3:236-249.
Bruinenberg PM, de Bot PHM, van Dijken JP, Scheffers WA: NADH-linked aldose reductase: the key to anaerobic fermentation of xylose by yeasts. Appl Microbiol Biotechnol 1984, 19:256-260.

(Continued)

*Primary Examiner* — Delia Ramirez
(74) *Attorney, Agent, or Firm* — Corey M. Crafton (57) ABSTRACT Recombinant genetic constructs and strains of *H. polymorpha* having significantly increased ethanol productivity with a simultaneous decreased production of xylitol during high-temperature xylose fermentation are disclosed. The constructs include a *H. polymorpha* XYL1 gene encoding xylose reductase mutated to decrease affinity of the enzyme toward NADPH. The modified version of XYL1 gene under control of a strong constitutive HpGAP promoter was overexpressed in a Δxyl1 background. A recombinant *H. polymorpha* strain overexpressing the mutated enzyme together with native xylitol dehydrogenase and xylulokinase in the Δxyl1 background was also constructed. Xylose consumption, ethanol and xylitol production by the constructed strain were evaluated during high-temperature xylose fermentation (48° C.). A significant increase in ethanol productivity (up to 7.4 times) was shown in the recombinant strain as compared with the wild type strain. Moreover, the xylitol production by the recombinant strain was reduced considerably: 0.9 mg$\chi$ (L$\chi$h)$^{-1}$ versus 4.2 mg$\chi$ (Lxh)$^{-1}$ by the wild type strain.

5 Claims, 7 Drawing Sheets (56) References Cited

OTHER PUBLICATIONS

Bruinenberg PM, Peter HM, van Dijken JP, Scheffers WA: The role of redox balances in the anaerobic fermentation of xylose by yeasts. Eur J Appl Microb Biotech 1983, 18:287-292.
Kotter P, Ciriacy M: Xylose fermentation by *Saccharomyces cerevisiae*. Appl Microbiol Biotechnol 1993, 38:776-783.
Walfridsson M, Anderlund M, Bao X, Hahn-Hagerdal B: Expression of different levels of enzymes from the Pichia stipitis XYL1 and XYL2 genes in *Saccharomyces cerevisiae* and its effects on product formation during xylose utilisation. Appl Microbiol Biotechnol 1997, 48:218-224.
Eliasson A, Hofmeyr JHS, Pedler S, Hahn-Hagerdal B: The xylose reductase/xylitol dehydrogenase/xylulokinase ratio affects product formation in recombinant xylose-utilising *Saccharomyces cerevisiae*. Enzyme Microb Technol 2001, 29:288-297 1:1.
Jin YS, Jeffries TW: Changing flux of xylose metabolites by altering expression of xylose reductase and xylitol dehydrogenase in recombinant *Saccharomyces cerevisiae*. Appl Biochem Biotechnol 2003, 105-108:277-286.
Karhumaa K, Fromanger R, Hahn-Hagerdal B, Gorwa-Grauslund MF: High activity of xylose reductase and xylitol dehydrogenase improves xylose fermentation by recombinant *Saccharomyces cerevisiae*. Appl Microbiol Biotechnol 2007, 73:1039-1046.
Jeppsson M, Bengtsson O, Franke K, Lee H, Hahn-Hagerdal B, Gorwa- Grauslund MF: The expression of a Pichia stipitis xylose reductase mutant with higher K(M) for NADPH increases ethanol production from xylose in recombinant *Saccharomyces cerevisiae* . Biotechnol Bioeng 2006, 93:665-673.
Petschacher B, Nidetzky B. Altering the coenzyme preference of xylose reductase to favor utilization of NADH enhances ethanol yield from xylose in a metabolically engineered strain of *Saccharomyces cerevisiae*. Microb. Cell Fact. 2008 7:9 doi:10.1186/1475-2859-7-9.
Jeppsson M, Johansson B, Hahn-Hagerdal B, Gorwa-Grauslund ME: Reduced oxidative pentose phosphate pathway flux in recombinant xylose-utilizing *Saccharomyces cerevisiae* strains improves the ethanol yield from xylose. Appl Environ Microbiol 2002, 68:1604-1609.
Verho R, Londesborough J, Penttila M, Richard P: Engineering redox cofactor regeneration for improved pentose fermentation in *Saccharomyces cerevisiae*. Appl Environ Microbiol 2003, 69:5892-5897.
Roca C, Nielsen J, Olsson L: Metabolic engineering of ammonium assimilation in xylose-fermenting *Saccharomyces cerevisiae* improves ethanol production. Appl Environ Microbiol 2003, 69:4732-4736.
van Maris AJA, Winkler AA, Kuyper M., de Laat WTAM, van Dijken JP, Pronk JT Development of Efficient Xylose Fermentation in *Saccharomyces cerevisiae*: Xylose Isomerase as a Key Component. Adv. Biochem. Engin. Biotechnol. 2007, 108:79-204.
Hahn-Hagerdal B, Wahibom CF, Gardonyi M, van Zyl WH, Cordero Otero RR, Jonsson LJ: Metabolic engineering of *Saccharomyces cerevisiae* for xylose utilization. Adv Biochem Eng Biotechnol 2001, 73:53-84.
Karhumaa K, Hahn-Hagerdal B, Gorwa-Grauslund MF: Investigation of limiting metabolic steps in the utilization of xylose by recombinant *Saccharomyces cerevisiae* using metabolic engineering. Yeast 2005, 22:359-368.
Ho NW, Chen Z, Brainard AP: Genetically engineered *Saccharomyces* yeast capable of effective cofermentation of glucose and xylose. Appl Environ Microbiol 1998, 64:1852-1859.
Ryabova OB, Chmil OM, Sibirny AA: Xylose and cellobiose fermentation to ethanol by the thermotolerant methylotrophic yeast *Hansenula polymorpha*. FEMS Yeast Res 2003, 4:157-164.
Voronovsky A, Ryabova O, Verba O, Ishchuk O, Dmytruk K, Sibirny A: Expression of xylA genes encoding xylose isomerases from *Escherichia coli* and *Streptomyces coelicolor* in the methylotrophic yeast *Hansenula polymorpha*. FEMS Yeast Res 2005, 5:1055-1062.
Dmytruk OV, Voronovsky AY, Abbas CA, Dmytruk KV, Ishchuk OP, Sibirny AA: Overexpression of bacterial xylose isomerase and yeast host xylulokinase improves xylose alcoholic fermentation in the thermotolerant yeast *Hansenula polymorpha*. FEMS Yeast Res 2008, 8:165-173.
Gellissen G: Hansenula polymorpha: Biology and Applications. Weinheim: Wiley-VCH; 2002, Chapters 7 & 8; pp. 95-123.
Ramezani-Rad M, Hollenberg CP, Lauber J, Wedler H, Griess E, Wagner C, Albermann K, Hani J, Piontek M, Dahlems U, Gellissen G: The Hansenula polymorpha (strain CBS4732) genome sequencing and analysis. FEMS Yeast Res 2003, 4:207-215.
Lahtchev KL, Semenova VD, Tolstorukov II, van der Klei I, Veenhuis M: Isolation and properties of genetically defined strains of the methylotrophic yeast *Hansenula polymorpha* CBS4732. Arch Microbiol 2002, 177:150-158.
Faber KN, Haima P, Harder W, Veenhuis M, Ab G: Highly-efficient electrotransformation of the yeast *Hansenula polymorpha*. Curr Genet 1994, 25:305-310.
Sohn JH, Choi ES, Kang HA, Rhee JS, Agaphonov MO, Ter-Avanesyan MD, Rhee SK: A dominant selection system designed for copy-number-controlled gene integration in Hansenula polymorpha Dl-1. Appl Microbiol Biotechnol 1999, 51:800-807.
Simpson FJ: D-xylulokinase. Methods in Enzymology 1966, 9:454-458.
Gonchar MV, Maidan MM, Sibirny AA: A new oxidaseperoxidase kit "Alcotest" for ethanol assays in alcoholic beverages. Food Technol Biotechnol 2001, 39:37-42.
Deschatelets L, Yu EK: A simple pentose assay for biomass conversion studies. Appl Microbiol Biotechnol 1986, 24:379-385.
Petschacher B, Leitgeb S, Kavanagh KL, Wilson DK, Nidetzky B: The coenzyme specificity of Candida tenuis xylose reductase (AKR2B5) explored by site-directed mutagenesis and X-ray crystallography. Biochem J 2005, 385:75-83.
Kaisa Karhumaa, Rosa Garcia Sanchez, Barbel Hahn-Hagerdal and Marie-F. Gorwa-Grauslund: Comparison of the xylose reductase-xylitol dehydrogenase and the xylose isomerase pathways for xylose fermentation by recombinant *Saccharomyces cerevisiae*. Microb. Cell Fact. 2007, 6:5 doi:10.1186/1475-2859-6-5.
Ishchuk OP, Voronovsky AY, Stasyk OV, Gayda GZ, Gonchar MV, Abbas CA, Sibirny AA. Improvement of xylose high-temperature fermentation in Hansenula polymorpha due to overexpression of the PDC1 gene coding for pyruvate decarboxylase. FEMS Yeast Res, 2008 (in press).
Dmytruk OV, Dmytruk KV, Abbas CA, Voronovsky AY, Sibirny AA. Engineering of xylose reductase and overexpression of xylitol dehydrogenase and xylulokinase improves xylose alcoholic fermentation in the thermotolerant yeast *Hansenula polymorpha*. Microbial Cell Factories, 7:21, Jul. 23, 2008.
Written Opinion of the International Searching Authority, PCT Application No. PCT/US2009/045813, Korean Intellectual Property Office, Feb. 2, 2010, Baek, Yeongran, pp. 1-3.
International Search Report, PCT Application No. PCT/US2009/045813, Korean Intellectual Property Office, Feb. 3, 2010, Baek, Yeongran, pp. 1-4.
Grabek-Lejko et al., Plate ethanol-screening assay for selection of the *Pichia stipitis* and *Hansenula polymorpha* yeast mutants with altered capability for xylose alcoholic fermentation, J. Ind. Microbial Biotechnol (2006)33:934-940.
The Hague, Supplementary European Search Report, Nov. 24, 2011. pp. 1-10.

\* cited by examiner

Fig. 1

```
Hansenula polymorpha--    332-TQRDILVIPKSNQKERLV  (SEQ.ID NO: 1)
Candida shehatae------    265-AQRGIAVIPKSNLPERLV
Pichia guilliermondii-    256-TQRGLAVIPKSNNPDRLL
Candida parapsilosis--    259-TQRGIAVIPKSNNPDRLA
Pichia stipitis-------    260-SQRGIAIIPKSNTVPRLL
Candida tenuis--------    264-AQRGIAVIPKSNLPERLV H.p mutant XR---------    332-TQRDILVIPRSDQKERLV  (SEQ.ID NO: 2)
```

Table 1. Strains and plasmids used in the present investigation.

| Strains | Genotype | Reference |
|---|---|---|
| CBS4732 | leu 2-2 | [26] |
| Δxyl1 | Δxyl1::LEU2Sc | [22] |
| XRn | Δxyl1, pX1N-Z (GAPp-XYL1-AOXt) | This study |
| XRm | Δxyl1, pX1M-Z (GAPp-XYL1mod-AOXt) | This study |
| XRn/XDH | Δxyl1, pX1N-Z-X2 (GAPp-XYL1-AOXt, GAPp-XYL2-XYL2t) | This study |
| XRm/XDH | Δxyl1, pX1M-Z-X2 (GAPp-XYL1mod-AOXt, GAPp-XYL2-XYL2t) | This study |
| XRn/XDH/XK | Δxyl1, pX1N-Z-X2 (GAPp-XYL1-AOXt, GAPp-XYL2-XYL2t), pGLG61/HpXYL3 (GAPp-XYL3-AOXt) | This study |
| XRm/XDH/XK | Δxyl1, pX1M-Z-X2 (GAPp-XYL1mod-AOXt, GAPp-XYL2-XYL2t), pGLG61/HpXYL3 (GAPp-XYL3-AOXt) | This study |

Fig. 4

Table 2. XR, XDH, XK activities, ethanol and xylitol productivity of H. polymorpha transformants and control strain

| Strain | Activity [U (mg protein $^{-1}$)] | | | | Productivity [mg (L h) $^{-1}$] | |
|---|---|---|---|---|---|---|
| | XR | | XDH | XK | Ethanol | Xylitol |
| | NADPH /K$_M$ (µM) | NADH /K$_M$ (µM) | | | | |
| XRn | 0.091±0.005 /9±0.5 | 0.016±0.001 /100±5.5 | 0.551±0.035 | - | 6.3 | 3.6 |
| XRm | 0.01±0.001 /152±8.4 | 0.014±0.001 /112±6.5 | 0.504±0.028 | - | 9.8 | 3.2 |
| XRn/XDH | - | - | 1.3±0.074 | - | 12 | 3.1 |
| XRm/XDH | - | - | 1.485±0.087 | - | 18.4 | 1.6 |
| XRn/XDH/XK | - | - | - | 0.375±0.021 | 13.8 | 2.8 |
| XRm/XDH/XK | - | - | - | 0.366±0.019 | 54.7 | 0.9 |
| CBS4732 | 0.034±0.025 /7±0.4 | 0.012±0.001 /85±4.7 | 0.697±0.049 | 0.156±0.009 | 7.5 | 4.2 |

XRn – transformant bearing normal XYL1 gene; XRm – transformant bearing modified XYL1 gene (XYL1m).
- not determined

Table 3. Ethanol productivity of *H. polymorpha* constructed and initial strain

| Strain | Ethanol productivity [g (L h) -1] |
|---|---|
| 2Et-/2xPDC1 | 0.04 |
| 2Et-/2xPDC1/XRm/XDH | 0.11 |

Fig. 6B

H. polymorpha Xyl1 - DNA sequence for XYLOSE REDUCTASE    SEQ. ID NO: 3
1934 bp

```
   1 TTTTTTGTGT ATCTGTTCGA TTTTCTTCTT GAGTTGTAGG CGTTCTTTAG TCTTCATTTT
  61 TACTCGAGGC TTCTGCTCTG CTTTGCTATT GAACTCAGCT TTTGAAACCC GAATGGGTAG
 121 TTCATCTGCA GGTCGAAGTT TTGTTTCATC CAATAGCTCA ATTGCGAGGT CACAGCTCTC
 181 CTCTTTTAGA TATTCTATTA GACAATCACC TTTGAAGTGG CCTCCGTCGT CTTTATACAT
 241 TTTGATTTTG GAGGACCCAG TGCGCAAATC CTGTGCAAGA ACTCCATACT TACCGAAAAC
 301 TGCCTCCAGT TCCTCGTAGG TGATATCTTG GGGGATCTGA CTTACATAAA TGCAAGTATT
 361 TCTGTTCCTC CGAAACTGCT TCAATTCCTC TTTCTCTTGC TTCAATTCAT CGAGCCGCTG
 421 ACGCTTCTCG CGTTTAAGAT ATTCAGAAGT GGTCACCTCA TCATGAGGCC TCTTCTCGGG
 481 CAGGTAATCC TGTATAACTG GTACCCAACG CTCTAGAATT GGATTGAACT CAAAGCACTC
 541 CTTTTCCTCG GGATTTTCAA TCACCCATCG AGCACGTACT TTATCAAAGA ATAAGTATGT
 601 TGCCAGATTC TGTGGCAGAT CCTCCGGAAG AGTGTTCTGT ATCTCATCGA TCAAGGGCAT
 661 GAGAATATGC ACACGCAGAT TAGCAAAAAT CTTGTATTAT TTTTTAGTGG CTGCACACCT
 721 CACACCGATT TCCCCGAAAT CGCTGCGAAT GAAGGCAGTG GTGGGGTACG TAATGTTGAG
 781 CTGAAACAGC AAACCTATAA ATTTGTGGGG GAATTTCCTA GAAAAAAGCA CCCTTGCCTA
 841 AAATTAGTTT TTAACTTTTT TCACTTTTTA GGAGAGATGG CTTCCAAGAC AATTAAGTTG
 901 AATAATGGCA TTGAAATCCC ACTAGTTGGG TTCGGCTGCT GGAAAGTCGA AAAGTCAATC
 961 TGTGCTGAGC AGATTTACGA GGCAATTAAA GTTGGTTACC GTCTGTTTGA TGGCGCAATG
1021 GACTATGGTA ATGAAAAGCA AATTGGCCAG GGAATTGCCA AGGCCATTGA AGATGGTTTG
1081 GTCAAGAGAG AGGAGCTGGT TATTGTTTCC AAGCTATGGA ACAATTATCA CAAGCCGGAG
1141 AATGTGAAGA AGGCAATTAG AAGAGTTCTT GACGACCTAA AATTGGATTA TTTGGATATT
1201 TACTACATCC ACTTCCCAAT TGCTCAAAAA TTTGTCCCAT TCGAGGAGAA ATACCCACCA
1261 GGGTTTTACT GTGGCCCTAA TGGTTGGGAG TTCGAGGACG TTCCGCTTGC CGTGACTTGG
1321 AGGGCAATGG AAGAACTTGT TGAGGAGGGG CTTGTCAAGT CAATTGGTAT CTCCAACTTC
1381 TCAGGTGCTT TGATCCAGGA CCTGCTGAGA GGTTGCAAGA TTAAGCCTCA ATTGCTTCAG
1441 ATTGAGCACC ATCCTTACCT CACTCAAGAG AAATTGATCA AGTACGTTCA GGCTCAGGAC
1501 ATTGCTGTTG TTGCCTACTC TTCATTTGGA CCACAGTCCT TTGTGGAGCT AGACCATGCT
1561 AAGGCCAAGA ACACTGTTTC TTTGCTCAAG CACGATCTGA TCAACAGCAT TGCTTCTGCT
1621 CACAAGGTCA CCCCTGCTCA GGTCCTCCTG AGATGGGCTA CCCAAAGAGA CATCTTGGTC
1681 ATTCCAAAGT CCAACCAAAA GGAGAGACTG GTCCAAAACC TGAAGGTCAA TGACTTCAAT
1741 CTGTCTGAGG AAGAGATCAA GCAAATCAGC TCTTTGAACC AGGATCTGAG ATTCAATGAT
1801 CCTTGGACCT GGAACGAAAT TCCAACCTTT ATCTAAACCT TTGAAGGAAT AGAGTGGTTT
1861 ACCCACAAAC TATCATTGTA GGATGGTGCG TAAATTTCCG TCAGTATGGC GAACGCAAGG
1921 TCTGTCCGCG AAAA
```

Fig. 7A

Figure  H. polymorpha Xyl1 - protein sequence for XYLOSE REDUCTASE    SEQ. ID NO: 4

389 aa

```
  1 MHTQISKNLV LFFSGCTPHT DFPEIAANEG SGGVRNVELK QQTYKFVGEF PRKKHPCLKL
 61 VFNFFHFLGE MASKTIKLNN GIEIPLVGFG CWKVEKSICA EQIYEAIKVG YRLFDGAMDY
121 GNEKQIGQGI AKAIEDGLVK REELVIVSKL WNNYHKPENV KKAIRRVLDD LKLDYLDIYY
181 IHFPIAQKFV PFEEKYPPGF YCGPNGWEFE DVPLAVTWRA MEELVEEGLV KSIGISNFSG
241 ALIQDLLRGC KIKPQLLQIE HHPYLTQEKL IKYVQAQDIA VVAYSSFGPQ SFVELDHAKA
301 KNTVSLLKHD LINSIASAHK VTPAQVLLRW ATQRDILVIP KSNQKERLVQ NLKVNDFNLS
361 EEEIKQISSL NQDLRFNDPW TWNEIPTFI
```

Fig. 7B

```
                        SEQUENCE LISTING

<160> NUMBER OF SEQ ID NOS: 9

<210> SEQ ID NO 1
<211> LENGTH: 18
<212> TYPE: PRT
<213> ORGANISM: H. polymorpha

<400> SEQUENCE: 1

Thr Gln Arg Asp Ile Leu Val Ile Pro Lys Ser Asn Gln Lys Glu Arg
1               5                   10                  15

Leu Val

<210> SEQ ID NO 2
<211> LENGTH: 18
<212> TYPE: PRT
<213> ORGANISM: H. polymorpha

<400> SEQUENCE: 2

Thr Gln Arg Asp Ile Leu Val Ile Pro Arg Ser Asp Gln Lys Glu Arg
1               5                   10                  15

Leu Val

<210> SEQ ID NO 3
<211> LENGTH: 1874
<212> TYPE: DNA
<213> ORGANISM: H. polymorpha

<400> SEQUENCE: 3 tttttgtgt atctgttcga ttttcttctt gagttgtagg cgttctttag tcttcatttt        60
tactcgaggc ttctgctctg ctttgctatt gaactcagct tttgaaaccc gaatgggtag      120
ttcatctgca ggtcgaagtt ttgtttcatc caatagctca attgcgaggt cacagctctc      180 ctctttaga tattctatta gacaatcacc tttgaagtgg cctccgtcgt ctttatacat       240
```

```
tttgattttg gaggacccag tgcgcaaatc ctgtgcaaga actccatact taccgaaaac    300
tgcctccagt tcctcgtagg tgatatcttg ggggatctga cttacataaa tgcaagtatt    360
tctgttcctc cgaaactgct tcaattcctc tttctcttgc ttcaattcat cgagccgctg    420
acgcttctcg cgtttaagat attcagaagt ggtcacctca tcatgaggcc tcttctcggg    480
caggtaatcc tgtataactg gtacccaacg ctctagaatt ggattgaact caaagcactc    540
cttttcctcg ggattttcaa tcacccatcg agcacgtact ttatcaaaga ataagtatgt    600
tgccagattc tgtggcagat cctccggaag agtgttctgt atctcatcga tcaagggcat    660
gagaatatgc acacgcagat tagcaaaaat cttgtattat tttttagtgg ctgcacacct    720
cacaccgatt tccccgaaat cgctgcgaat gaaggcagtg gtggggtacg taatgttgag    780
ctgaaacagc aaacctataa atttgtgggg gaatttccta gaaaaaagca cccttgccta    840
aaattagttt ttaactttttt tcactttttta ggagagatgg cttccaagac aattaagttg    900
aataatggca ttgaaatccc actagttggg ttcggctgct ggaaagtcga aaagtcaatc    960
tgtgctgagc agatttacga ggcaattaaa gttggttacc gtctgtttga tggcgcaatg   1020
gtcaagagag aggagctggt tattgtttcc aagctatgga acaattatca caagccggag   1080
aatgtgaaga aggcaattag aagagttctt gacgacctaa aattggatta tttggatatt   1140
tactacatcc acttcccaat tgctcaaaaa tttgtcccat cgaggagaa atacccacca    1200
gggttttact gtgccctaa tggttgggag ttcgaggacg ttccgcttgc cgtgacttgg   1260
agggcaatgg aagaacttgt tgaggagggg cttgtcaagt caattggtat ctccaacttc   1320
tcaggtgctt tgatccagga cctgctgaga ggttgcaaga ttaagcctca attgcttcag   1380
attgagcacc atccttacct cactcaagag aaattgatca agtacgttca ggctcaggac   1440
attgctgttg ttgcctactc ttcatttgga ccacagtcct tgtggagct agaccatgct   1500
aaggccaaga acactgtttc tttgctcaag cacgatctga tcaacagcat tgcttctgct   1560
cacaaggtca cccctgctca ggtcctcctg agatgggcta cccaaagaga catcttggtc   1620
attccaaagt ccaaccaaaa ggagagactg gtccaaaacc tgaaggtcaa tgacttcaat   1680
ctgtctgagg aagagatcaa gcaaatcagc tctttgaacc aggatctgag attcaatgat   1740
ccttggacct ggaacgaaat tccaaccttt atctaaacct ttgaaggaat agagtggttt   1800
acccacaaac tatcattgta ggatggtgcg taaatttccg tcagtatggc gaacgcaagg   1860
tctgtccgcg aaaa                                                    1874

<210> SEQ ID NO 4
<211> LENGTH: 389
<212> TYPE: PRT
<213> ORGANISM: H. polymorpha

<400> SEQUENCE: 4

Met His Thr Gln Ile Ser Lys Asn Leu Val Leu Phe Phe Ser Gly Cys
1               5                   10                  15

Thr Pro His Thr Asp Phe Pro Glu Ile Ala Ala Asn Glu Gly Ser Gly
            20                  25                  30

Gly Val Arg Asn Val Glu Leu Lys Gln Gln Thr Tyr Lys Phe Val Gly
        35                  40                  45

Glu Phe Pro Arg Lys Lys His Pro Cys Leu Lys Leu Val Phe Asn Phe
    50                  55                  60

Phe His Phe Leu Gly Glu Met Ala Ser Lys Thr Ile Lys Leu Asn Asn
65                  70                  75                  80
```

```
Gly Ile Glu Ile Pro Leu Val Gly Phe Gly Cys Trp Lys Val Glu Lys
             85                  90                  95

Ser Ile Cys Ala Glu Gln Ile Tyr Glu Ala Ile Lys Val Gly Tyr Arg
            100                 105                 110

Leu Phe Asp Gly Ala Met Asp Tyr Gly Asn Glu Lys Gln Ile Gly Gln
            115                 120                 125

Gly Ile Ala Lys Ala Ile Glu Asp Gly Leu Val Lys Arg Glu Glu Leu
            130                 135                 140

Val Ile Val Ser Lys Leu Trp Asn Asn Tyr His Lys Pro Glu Asn Val
145                 150                 155                 160

Lys Lys Ala Ile Arg Arg Val Leu Asp Asp Leu Lys Leu Asp Tyr Leu
                165                 170                 175

Asp Ile Tyr Tyr Ile His Phe Pro Ile Ala Gln Lys Phe Val Pro Phe
            180                 185                 190

Glu Glu Lys Tyr Pro Pro Gly Phe Tyr Cys Gly Pro Asn Gly Trp Glu
            195                 200                 205

Phe Glu Asp Val Pro Leu Ala Val Thr Trp Arg Ala Met Glu Glu Leu
            210                 215                 220

Val Glu Glu Gly Leu Val Lys Ser Ile Gly Ile Ser Asn Phe Ser Gly
225                 230                 235                 240

Ala Leu Ile Gln Asp Leu Leu Arg Gly Cys Lys Ile Lys Pro Gln Leu
                245                 250                 255

Leu Gln Ile Glu His His Pro Tyr Leu Thr Gln Glu Lys Leu Ile Lys
            260                 265                 270

Tyr Val Gln Ala Gln Asp Ile Ala Val Val Ala Tyr Ser Ser Phe Gly
            275                 280                 285

Pro Gln Ser Phe Val Glu Leu Asp His Ala Lys Ala Lys Asn Thr Val
            290                 295                 300

Ser Leu Leu Lys His Asp Leu Ile Asn Ser Ile Ala Ser His Lys
305                 310                 315                 320

Val Thr Pro Ala Gln Val Leu Leu Arg Trp Ala Thr Gln Arg Asp Ile
                325                 330                 335

Leu Val Ile Pro Lys Ser Asn Gln Lys Glu Arg Leu Val Gln Asn Leu
            340                 345                 350

Lys Val Asn Asp Phe Asn Leu Ser Glu Glu Ile Lys Gln Ile Ser
                355                 360                 365

Ser Leu Asn Gln Asp Leu Arg Phe Asn Asp Pro Trp Thr Trp Asn Glu
            370                 375                 380

Ile Pro Thr Phe Ile
385

<210> SEQ ID NO 5
<211> LENGTH: 18
<212> TYPE: PRT
<213> ORGANISM: Candida shehatae

<400> SEQUENCE: 5

Ala Gln Arg Gly Ile Ala Val Ile Pro Lys Ser Asn Leu Pro Glu Arg
1               5                   10                  15

Leu Val

<210> SEQ ID NO 6
<211> LENGTH: 18
<212> TYPE: PRT
<213> ORGANISM: Pichia guilliermondii
```

```
<400> SEQUENCE: 6

Thr Gln Arg Gly Leu Ala Val Ile Pro Lys Ser Asn Asn Pro Asp Arg
1               5                   10                  15

Leu Leu

<210> SEQ ID NO 7
<211> LENGTH: 18
<212> TYPE: PRT
<213> ORGANISM: Candida parapsilosis

<400> SEQUENCE: 7

Thr Gln Arg Gly Ile Ala Val Ile Pro Lys Ser Asn Asn Pro Asp Arg
1               5                   10                  15

Leu Ala

<210> SEQ ID NO 8
<211> LENGTH: 18
<212> TYPE: PRT
<213> ORGANISM: Pichia stipitis

<400> SEQUENCE: 8

Ser Gln Arg Gly Ile Ala Ile Ile Pro Lys Ser Asn Thr Val Pro Arg
1               5                   10                  15

Leu Leu

<210> SEQ ID NO 9
<211> LENGTH: 18
<212> TYPE: PRT
<213> ORGANISM: Candida tenuis

<400> SEQUENCE: 9

Ala Gln Arg Gly Ile Ala Val Ile Pro Lys Ser Asn Leu Pro Glu Arg
1               5                   10                  15

Leu Val
```

ENGINEERING OF XYLOSE REDUCTASE AND OVEREXPRESSION OF XYLITOL DEHYDROGENASE AND XYLULOKINASE IMPROVES XYLOSE ALCOHOLIC FERMENTATION IN THE THERMOTOLERANT YEAST *HANSENULA POLYMORPHA*

PRIORITY AND INCORPORATION BY REFERENCE

This application is a 35 U.S.C. §371 national phase entry of International Application No. PCT/US2009/045813 filed Jun. 1, 2009, which claims priority to U.S. provisional application No. 61/057,515 filed May 30, 2008, which is incorporated by reference in its entirety, including all references cited therein (repeated herein) to the extent such references aid in understanding the invention or in obtaining the materials and methods that would facilitate the practice of the invention. If the content of a cited reference conflicts with teaching of the present application, the present application shall be deemed to control the understanding.

TECHNICAL FIELD

This application relates to the field of cellulosic ethanol production by fermentation, particularly to fermentation of xylose containing sources, more particularly to recombinant *H. polymorpha* strains useful for the production of ethanol by fermentation of xylose, and still more particularly to strains of *H. polymorpha* that overexpress a mutant *H. polymorpha* xylose reductase having altered affinity for NADPH together with either endogenous or recombinant xylose dehydrogenase and xylulokinase, that achieve enhanced ethanol production by fermentation on xylose containing media.

BACKGROUND

Ethanol produced from lignocellulosics is an environmentally friendly alternative to fossil fuels. As a substantial fraction of lignocellulose material consists of xylose, it is necessary to ferment efficiently xylose to ethanol to make the process cost-effective [1].

Some yeasts, filamentous fungi and bacteria are able to convert xylose to ethanol. Yeasts and most of other fungi first reduce xylose to xylitol using xylose reductase, which strongly prefers NADPH as coenzyme, EC 1.1.1.21 (XR). Then they oxidize xylitol to xylulose with strictly NAD-dependent xylitol dehydrogenase, EC 1.1.1.9 (XDH) [2]. The difference in cofactor specificity results in redox imbalance that leads to decreasing ethanol production and accumulation of xylitol [3, 4, 5, 6, 7, 8]. The xylitol production has been reduced by metabolic engineering directed to optimize the expression levels of XR and XDH [9, 10, 11, 12], change the cofactor specificity of XR from NADPH to NADH [13, 13a], or modify the redox metabolism of the host cell [14, 15, 16]. The other used approach to bypass redox imbalance during xylose fermentation was based on expression of fungal or bacterial xylose isomerase, EC 5.3.1.5 (XI) which converts xylose directly to xylulose and does not require redox cofactors [17, 18]

The additional overexpression of xylulokinase, EC 2.7.1.17 (XK) (the third enzyme in the xylose metabolism) that converts xylulose to xylulose-5-phosphate, which enters the pentose phosphate pathway and then into the central metabolism, has been shown to enhance both aerobic and anaerobic xylose utilization in XR-XDH- as well as XI carrying strains [12, 19]. Overexpression of XK is necessary to overcome the naturally low expression level of this enzyme [3, 5]. The overexpression resulted in more efficient conversion of xylose to ethanol [5, 20].

The thermotolerant methylotrophic yeast *Hansenula polymorpha* is capable of alcoholic fermentation of xylose at elevated temperatures (45-48° C.) [21, 22, 23]. This property of *H. polymorpha* makes it a good candidate for use in an efficient process of simultaneous saccharification and fermentation (SSF). SSF combines enzymatic hydrolysis of lignocellulosic material with subsequent fermentation of released sugars in the same vessel. Major advantages of exploring the utility of *H. polymorpha* for ethanol production from cellulosic material using are this yeast has (i) well developed methods of molecular genetics and (ii) the availability of a whole genome sequence for a model strain CBS4732 [24; 25].

SUMMARY

The present disclosure describes the construction of recombinant *H. polymorpha* strains that overexpress a modified XR (K341R N343D) together with native XDH and XK on the Δxyl1 background. Xylose consumption, ethanol and xylitol production of the strain in comparison with those of strains overexpressing the native XR, XDH and XK are presented for comparison to demonstrate that overexpression of the altered XR enzyme enhances ethanol yield when the *H. polymorpha* strain is grown on media containing xylose. Related recombinant nucleic acids, the mutant enzyme, and methods of using the same for ethanol fermentation on xylose are also disclosed herein.

DESCRIPTION OF THE DRAWINGS

FIG. 1. Linear schemes of the plasmids used in this disclosure: pX1M-Z, pX1N-Z, pX1M-Z-X2, pX1N-Z-X2 and pGLG61/HpXYL3. Expression cassettes prGAP-XYL1-trAOX, prGAP-XYL2-trXYL2 and prGAP-XYL3-trAOX are shown as white, gray and doted boxes, respectively. The modified version of XYL1 ORF is shown as black box. The zeocin resistance gene (Zeo$^r$) and geneticin resistance gene (APH), linked to an impaired constitutive gene promoter, encoding glyceraldehydephosphate dehydrogenase (GAP) are designated with the hatched lines. *H. polymorpha* LEU2 gene and the telomeric region (TEL188) [29] as an autonomously replicating sequence are shown as cross-hatched lines. Origin of replication ORI and ampicillin resistance gene (bla)-arrows. Restriction sites: P, PstI; H, HindIII; S, SacI; SI, SalI; B, BamHI; ScII, SacII; Xb, XbaI; RI, EcoRI; NdI, NdeI; N, NotI.

FIG. 7. FIG. 7A shows the DNA sequence for the cloned *H. polymorpha* xyl1 gene encoding xylose reductase with the start and stop cordons highlighted. FIG. 7B shows the protein sequence for the cloned *H. polymorpha* xylose reductase protein with the NADPH binding site prior to mutagenesis being highlighted.

DETAILED DESCRIPTION OF METHODS, STRAINS, AND RESULTS

Strains and Media

Yeast strains *H. polymorpha* CBS4732s (leu2-2) [26], Δxyl1 [22] and transformants (Table 1) were grown on YPD (0.5% yeast extract, 1% peptone, 2% glucose) or minimal medium (0.67% YNB without amino acids, 4% xylose or 2% glucose) at 37° C. For the CBS4732s strain leucine (40 mg $L^{-1}$) was supplemented into the medium. For selection of yeast transformants on YPD, 130-150 mg $L^{-1}$ of zeocin or 0.5-0.6 mg $L^{-1}$ of G418 were added.

The *E. coli* DH5α strain (Φ80dlacZΔM15, recA1, endA1, gyrA96, thi-1, hsdR17($r_K^-$, $m_K^+$), supE44, relA1, deoR, Δ(lacZYA-argF)U169) was used as a host for propagation of plasmids. The strain DH5α was grown at 37° C. in LB medium as described previously [27]. Transformed *E. coli* cells were maintained on a medium containing 100 mg $L^{-1}$ of ampicillin.

Molecular-Biology Techniques

Standard cloning techniques were applied [27]. Genomic DNA of *H. polymorpha* was isolated using the Wizard® Genomic DNA Purification Kit (Promega, Madison, Wis., USA). Restriction endonucleases and DNA ligase (Fermentas, Vilnius, Lithuania) were used according to the manufacturer specifications. Plasmid isolation from *E. coli* was performed with the Wizard® Plus SV Minipreps DNA Purification System (Promega, Madison, Wis., USA). PCR-amplification of the fragments of interest was done with Platinum® Taq DNA Polymerase High Fidelity (Invitrogen, Carlsbad, Calif., USA) according to the manufacturer specification. PCRs were performed in GeneAmp® PCR System 9700 thermocycler (Applied Biosystems, Foster City, Calif., USA). Transformation of the yeast *H. polymorpha* by electroporation was carried out as described previously [28].

Plasmid Construction

Figure 1:
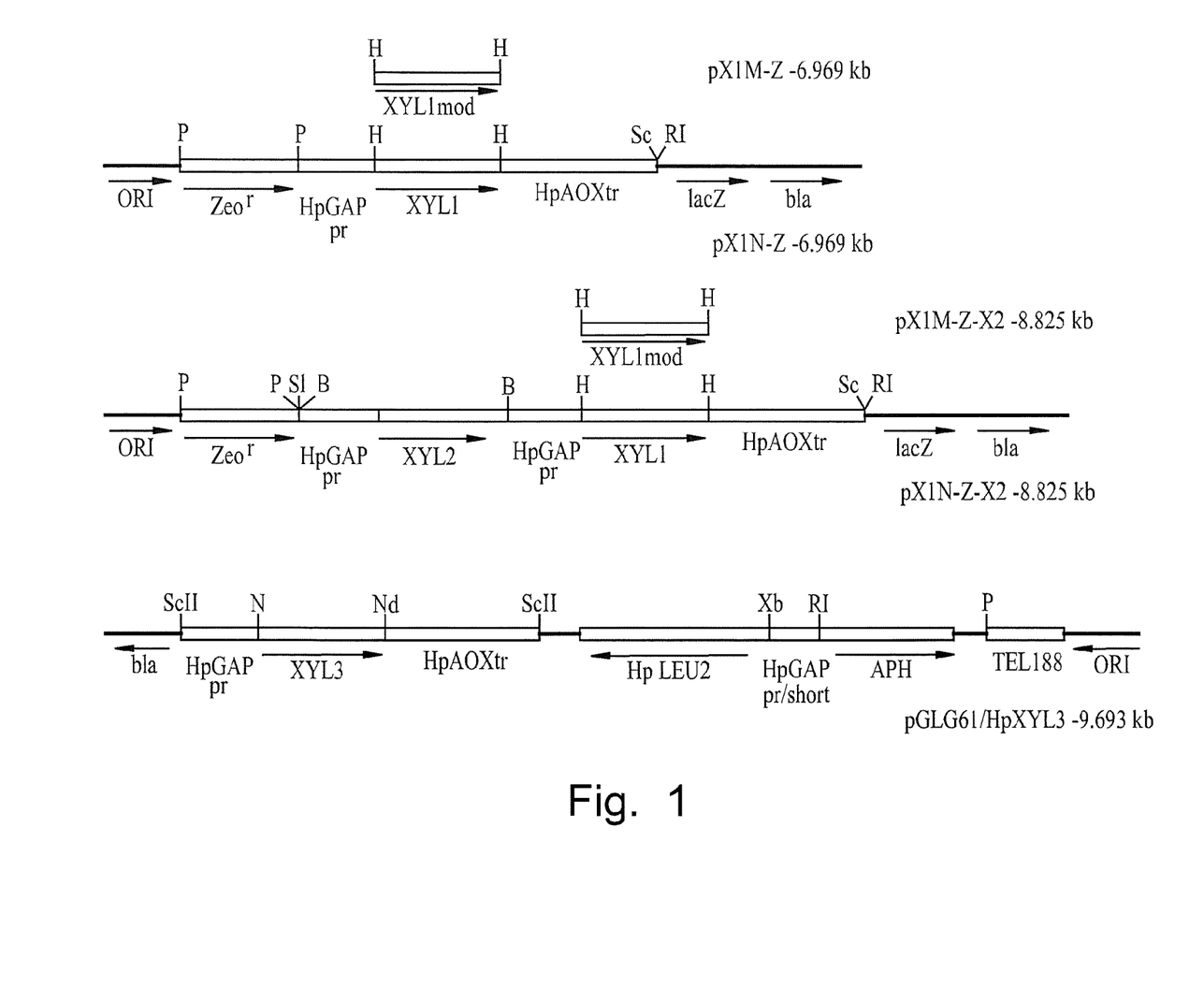

Recombinant plasmids pX1N-Z and pX1M-Z bearing native and modified version of XR, respectively, were constructed on the basis of the plasmid pUC57 (Fermentas, Vilnius, Lithuania). BamHI/SacI fragment with the HpGAP promoter and HpAOX terminator from the plasmid pKO8-GAPpr [22] was cloned into the BamHI-SacI digested plasmid pUC57 with preliminary eliminated restriction sites NdeI and HindIII. In the resulting plasmid restriction sites NdeI and NotI located between the HpGAP promoter and HpAOX terminator were removed and the unique HindIII site arose. The ORF of XYL1 was PCR-amplified from genomic DNA of CBS4732 using pair of primers HpX1for (SEQ ID NO: 10) (CCC AAG CTT ATG CAC ACG CAG ATT AGC AAA AAT CTT G) and HpX1rev (SEQ ID NO: 11) (CGC AAG CTT TTA GAT AAA GGT TGG AAT TTC GTT CCA GGT CC) and cloned into the HindIII site to create expression cassette prGAP-XYL1-trAOX (restriction sites are italicized in all primers). Modification of XR gene was performed via the overlap PCR. The pairs of primers HpXlMfor (SEQ ID NO: 12) (CAT CTT GGT CAT TCC AAG GTC CGA CCA AAA GGA GAG ACT G) and HpX1Mrev (SEQ ID NO: 13) (CAG TCT CTC CTT TTG GTC GGA CCT TGG AAT GAC CAA GAT G) were used to produce K341→R and N343→D substitutions in resulting modified XR (mismatched bases for the mutation are shown in bold). Primers HpX1for and HpX1rev were used for cloning of modified version of XR gene as described above for the native gene. The yeast selective marker conferring resistance to zeocin was PCR-amplified from the plasmid pPICZB (Invitrogen) using pair of primers Ko58 (SEQ ID NO: 14) (CGG GGT ACC TG CAG ATA ACT TCG TAT AGC ATA C) and Ko59 (SEQ ID NO: 15) (CGG GGT ACC TG CAG TAA TTC GCT TCG GAT AAC) and cloned into the PstI linearzed vectors creating pX1N-Z or pX1M-Z (FIG. 1).

The *H. polymorpha* XYL2 gene with own terminator and the HpGAP promoter were amplified from the genomic DNA of CBS4732 using the corresponding pairs of primers L1 (SEQ ID NO: 16) (CTC GGA TCC CAA TTA TCA TTA ATA ATC)/Ko135 (SEQ ID NO: 17) (CAG CAG AAG GAT TGT TCA TTT TGT TTC TAT ATT ATC) and Ko134 (SEQ ID NO: 18) (GAT AAT ATA GAA ACA AAA TGA ACA ATC CTT CTG CTG)/Ko133 (SEQ ID NO: 19) (ACA GGA TCC ATC CAT GAG AAA CG). Primers L1 and Ko133 were used for obtaining the fragment containing the XYL2 gene with own terminator driven with the HpGAP promoter by the overlap PCR. This fragment was cloned into the BamHI linearized plasmids pX1N-Z i pX1M-Z, resulting in the recombinant constructs pX1N-Z-X2 and pX1M-Z-X2, respectively (FIG. 1).

The expression cassette containing prGAP-XYL3-trAOX was obtained as SacII restriction fragment from the plasmid pKO8/GAP/HpXYL3 [23] and cloned into the SacII linearized plasmids pGLG61 [29]. The resulting plasmid was designated pGLG61/HpXYL3 (FIG. 1). The accuracy of constructed plasmids was verified by sequencing. Constructed plasmids are presented in Table 1.

Biochemical Methods

The XR activity in cell extracts was determined spectrophotometrically at 37° C. The XR assay mixture contained: Tris-HCl buffer (pH 7.0) 100 mM, NADPH 0.15 mM and xylose 350 mM. The reaction was started with cell extract addition [3]. To evaluate $K_M$ towards NADPH or NADH the XR activities were measured with four different concentrations of cofactors 20, 50, 100 and 150 µM (each in triplicate).

The XDH activity in cell extracts was determined spectrophotometrically at 37° C. The XDH assay mixture contained: Tris-HCl buffer (pH 8.8) 100 mM, $MgCl_2$ 10 mM, NAD 3 mM and xylitol 300 mM. The reaction was started with cell extract addition [3].

The XK activity in cell extracts was determined spectrophotometrically at 37° C. as was described before [30], with some modifications. The XK assay mixture contained: Tris-HCl buffer (pH 7.8) 50 mM, $MgCl_2$ 5 mM, NADH 0.2 mM, phosphoenolpyruvate 1 mM, D-xylulose 8.5 mM, lactate dehydrogenase (EC 1.1.1.27) (Fluka, St. Louis, Mo., USA) 10 U, pyruvate kinase (EC 2.7.1.40) (Fluka, St. Louis, Mo., USA) 0.05 U, and ATP 2 mM. The reaction was started with addition of cell extract. For the XK assay, another blank without pyruvate kinase and lactate dehydrogenase was used to minimize the interference of XDH activity in *H. polymorpha*.

All assay experiments were repeated at least twice.

Analyses

Cells of transformants were grown in the rich YPX medium (1% yeast extract, 2% peptone, 4% xylose) during 2 days and inoculated into the YNB medium with 12% xylose. Fermentation was carried out at the temperature of 48° C. with limited aeration (140 revolutions×min$^{-1}$). Concentrations of ethanol in medium were determined using alcohol oxidase/peroxidase-based enzymatic kit "Alcotest" [31]. Concentrations of xylitol in medium were determined enzymaticaly as described earlier (Enzymatic determination of D-sorbitol and xylitol, R-Biopharm GmbH, Darmstadt, Germany) with slight modifications. Nitrotetrazolium Blue (NTB) 12 mM and phenazine methosulfate 15 mM were used instead iodonitrotetrazolium chloride and diaphorase, respectively. The absorbance of the reduced NTB was measured at 570 nm. Concentrations of xylose from fermentation in mineral medium were analyzed by chemical method as was described before [32].

Experiments were performed at least twice.

Results

Engineering of XR

Figure 2:
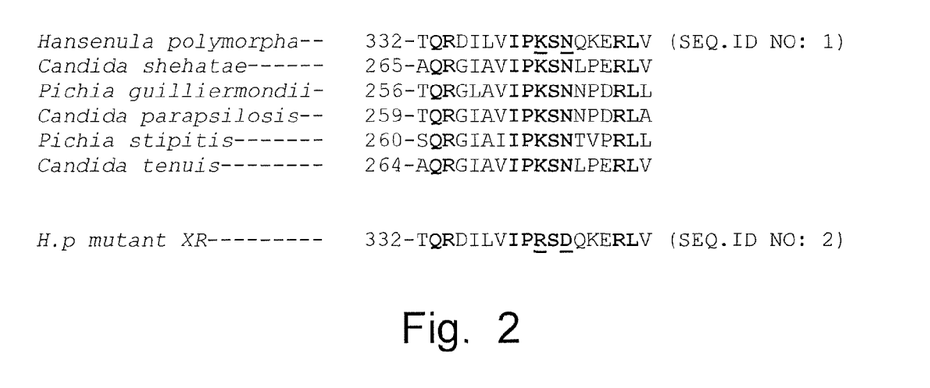
FIG. 2. Alignment of XRs cofactor binding site sequences from several xylose-utilizing yeast against *H. polymorpha* XYL1 sequence. Conserved sequences are in bold. Underlined amino acids were changed (K→R and N→D).
The comparative XR sequences are from *Hansenula polymorpha* (SEQ. ID NO:1), *Candida shehatae* (SEQ. ID NO:5), *Pichia guilliermondii* (SEQ. ID NO:6), *Candida parapsilosis* (SEQ. ID NO:7), *Pichia Stipitis* (SEQ. ID NO:8), *Candida tenuis* (SEQ. ID NO:9), and H.p. mutant XR (SEQ. ID NO:2).

To improve alcoholic fermentation of xylose and decrease xylitol formation, XR of *H. polymorpha* has been subjected to site-specific mutagenesis to reduce its affinity for NADPH. The amino acid sequence of the cofactor binding site of *H. polymorpha* XR (SEQ ID NO: 1) shows strict homology to the corresponding site of other xylose-utilizing yeasts (FIG. 2). In the present work the inventors substitute lysine and asparagine for arginine and aspartic acid at amino-acid positions 341 and 343, respectively to obtain a mutated *H. polymorpha* XR protein having the cofactor binding site of SEQ. ID NO: 2. These substitutions resemble those developed for successful modification of XR cofactor specificity in *Candida tenuis* [33].

Strain Construction

To generate strains with overexpression of native or modified versions of XR or strains with simultaneous overexpression of native or modified XR together with XDH, the *H. polymorpha* Δxyl1 [22] strain was transformed with SacI linearized plasmids pX1N-Z and pX1M-Z or pX1N-Z-X2 and pX1M-Z-X2, respectively. The transformants were grown on YPD medium supplemented with zeocin. The presence of expression cassettes in the transformants was examined by PCR using corresponding primers. To express the XK, the recombinant plasmid pGLG61/HpXYL3 was transformed into the recipient strain *H. polymorpha* overexpressing native or modified versions of XR and XDH. The transformants were grown on YPD medium in the presence of increasing concentrations of G418. The highest concentration of G418, which allows the transformants to grow, was 0.4 mg×ml$^{-1}$. Colonies able to grow on the selective medium appeared after 3 days of incubation with frequency of up to 20 transformants×mg$^{-1}$ DNA. The transformants were stabilized by cultivation in non-selective media for 10-12 generations with further shifting to the selective media with G418. The presence of recombinant XYL3 gene driven by the HpGAP promoter in genomic DNA of stable transformants was proven by PCR. As pGLG61-based plasmids promote multiple integration into the genome of recipient strains [29], constructed strains were examined by Southern hybridisation to select recombinant strains with equal amount of XK expression cassette. The strains bearing 3 copies of XK expression cassette were selected (data not shown). Constructed yeast strains are represented in Table 1.

Biochemical Analysis of Constructed Strains

Biochemical properties of XR in one of constructed recombinant strains (designated XRm) were studied. Specific activities of XR (with both cofactors NADPH and NADH), XDH and XK as well as affinities of native XR (XRn) and engineered XRm were measured (Table 2). XRm was characterized by $K_M$ of 152 μM for NADPH using xylose as a substrate, which is 17 times higher than the $K_M$ for NADPH of the native XR (9 μM). The $K_M$ of engineered XRm for NADH remained nearly unchanged (112 μM). Specific activity of XR with NADPH in the XRm strain decreased 4.8 times compared with the strain overexpressing native XR. The specific activity of XR with NADH in both strains remained unchanged. Strains XRn/XDH and XRm/XDH with additional overexpressing XDH possessed two-fold increase in the specific activity of XDH compared with the wild type strain. Overexpression of XK in strains XRn/XDH/XK and XRm/XDH/XK resulted in up to 2.4-fold increase in specific activity of XK as compared to CBS4732 (Table 2).

Xylose Fermentation

Figure 3A:
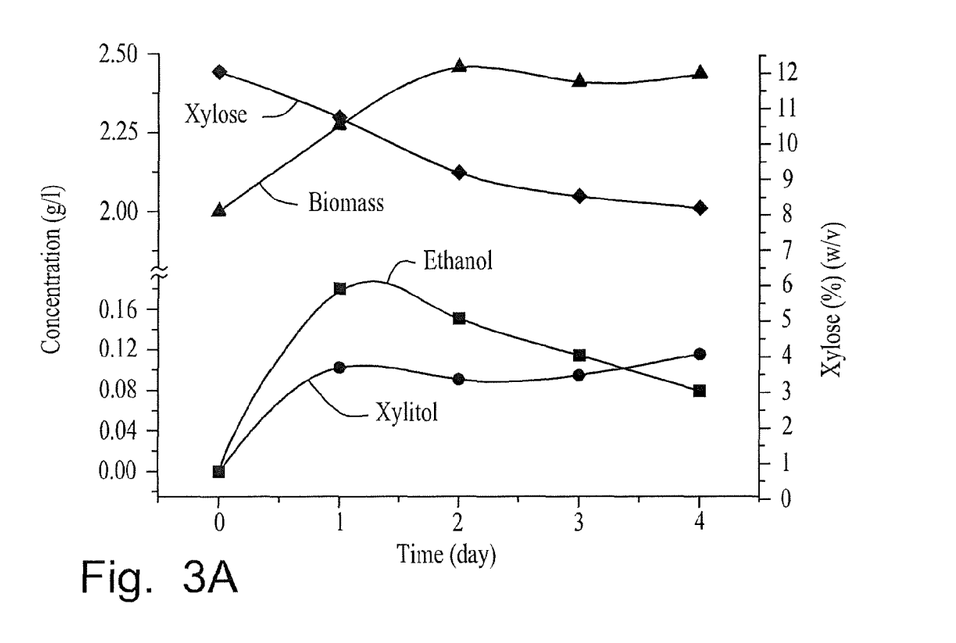
FIG. 3. Comparison of xylose fermentations at 48° C. by CBS4732 (A), XRn/XDH/XK (B) and XRm/XDH/XK (C). Symbols: ethanol (■), xylitol (●). biomass (▲) and xylose (♦).
Figure 3B:
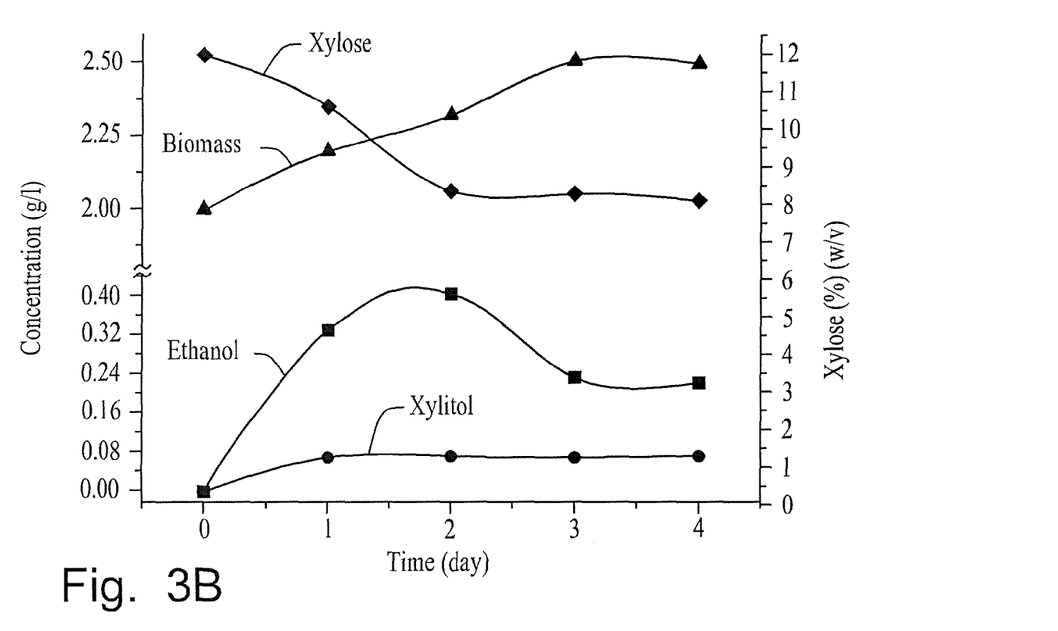
Figure 3C:
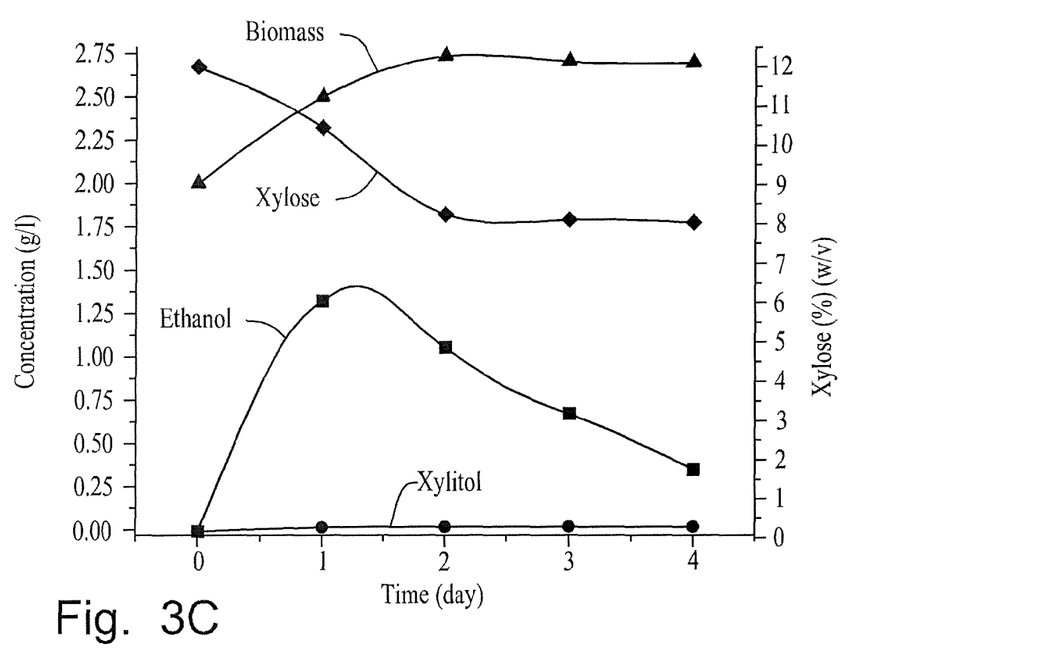
Figure 4:
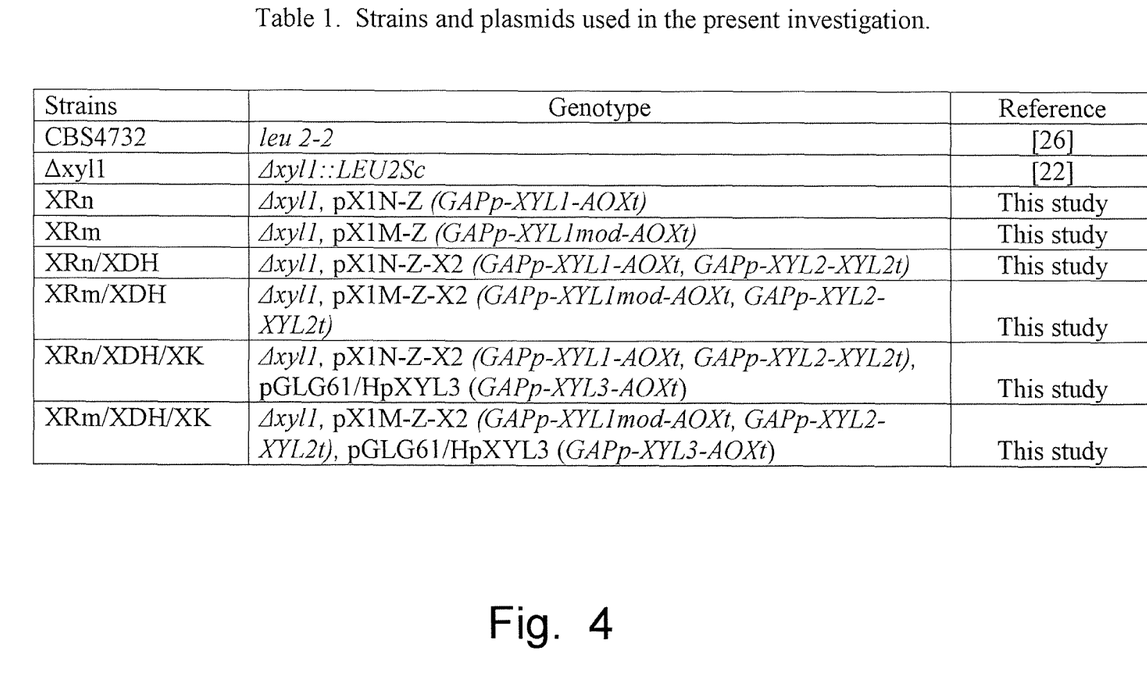
FIG. 4. Table 1 showing strains and plasmids used in the present disclosure.

Xylose fermentation by the constructed strains was compared in batch cultures with limited aeration. A mineral medium containing xylose (12%) and initial biomass concentration 2 g (dry weight)×L$^{-1}$ were used. Results of ethanol and xylitol production by the constructed strains are shown in Table 2. Ethanol productivity of the XRm strain was 9.8 mg×(L×h)$^{-1}$, which is 1.5- and 1.3-fold higher than the productivity of the XRn and the wild-type strain CBS4732, respectively. Xylitol production of these strains varied insignificantly. Ethanol productivity of the strain XRm/XDH (18.4 mg×(L×h)$^{-1}$) was increased 1.5 and 2.4 times as compared to XRn/XDH and CBS4732, respectively. Strain XRm/XDH possessed 1.3- and 2.6-fold reduction in xylitol production compared with XRn/XDH and CBS4732 strains. Ethanol productivity of the strain XRm/XDH/XK (54.7 mg×(L×h)$^{-1}$) was 4- and 7.4-fold higher compared to those of the strain XRn/XDH/XK (13.8 mg×(L×h)$^{-1}$) and CBS4732 (7.5 mg×(L×h)$^{-1}$). The xylitol production of the strain XRm/XDH/XK was significantly reduced to 0.9 mg×(L×h)$^{-1}$, which is 4.7- and 3-fold lower than those of the XRn/XDH/XK and control strain, respectively. Representative fermentation profiles for the strains XRn/XDH/XK, XRm/XDH/XK and CBS4732 are shown in FIG. 3. It has to be mentioned, that the consumption of xylose by *H. polymorpha* strains during the fermentation is low. Ethanol produced in the initial stage of xylose fermentation is reutilized after 1-2 days of the fermentation.

Expression of the XR mutant, XD, and XK Genes in a *H. polymorpha* Strain That Over Expresses Pyruvate Decarboxylase for Improved Alcoholic Fermentation of Xylose at Elevated Temperature (48° C.)

To improve alcoholic fermentation of xylose the engineered version of xylose reductase (XR) together with native xylitol dehydrogenase (XDH) were overexpressed in a recombinant *H. polymorpha* strain with an elevated level of pyruvate decarboxylase activity. Construction and biochemical characteristics of the initial strain 2Et⁻/2×PDC1 have been described earlier [35, 36].

To generate strains with simultaneous overexpression of modified versions of XR together with XDH, the *H. polymorpha* 2Et⁻/2×PDC1 strain was transformed with SacI linearized plasmid pX1M-Z-X2 (FIG. 1) [37]. Transformants were grown on YPD medium supplemented with zeocin (150 mg×L⁻¹). Colonies able to grow on the selective medium appeared after 3 days of incubation with frequency of up to 40 transformants×mg⁻¹ DNA. The transformants were stabilized by cultivation in non-selective medium for 10-12 generations with further shifting to the selective medium with zeocin. The presence of expression cassettes in the transformants was examined by PCR using primers L1/HpX1rev for the expression cassette bearing modified XYL1 gene under the control of strong constitutive promoter HpGAP and primers L1/Ko133 for the expression cassette bearing XYL2 gene under the same promoter. The sequences of used primers as well as modification of XYL1 gene are described in the article Dmytruk O. et al. [37].

Figure 5:
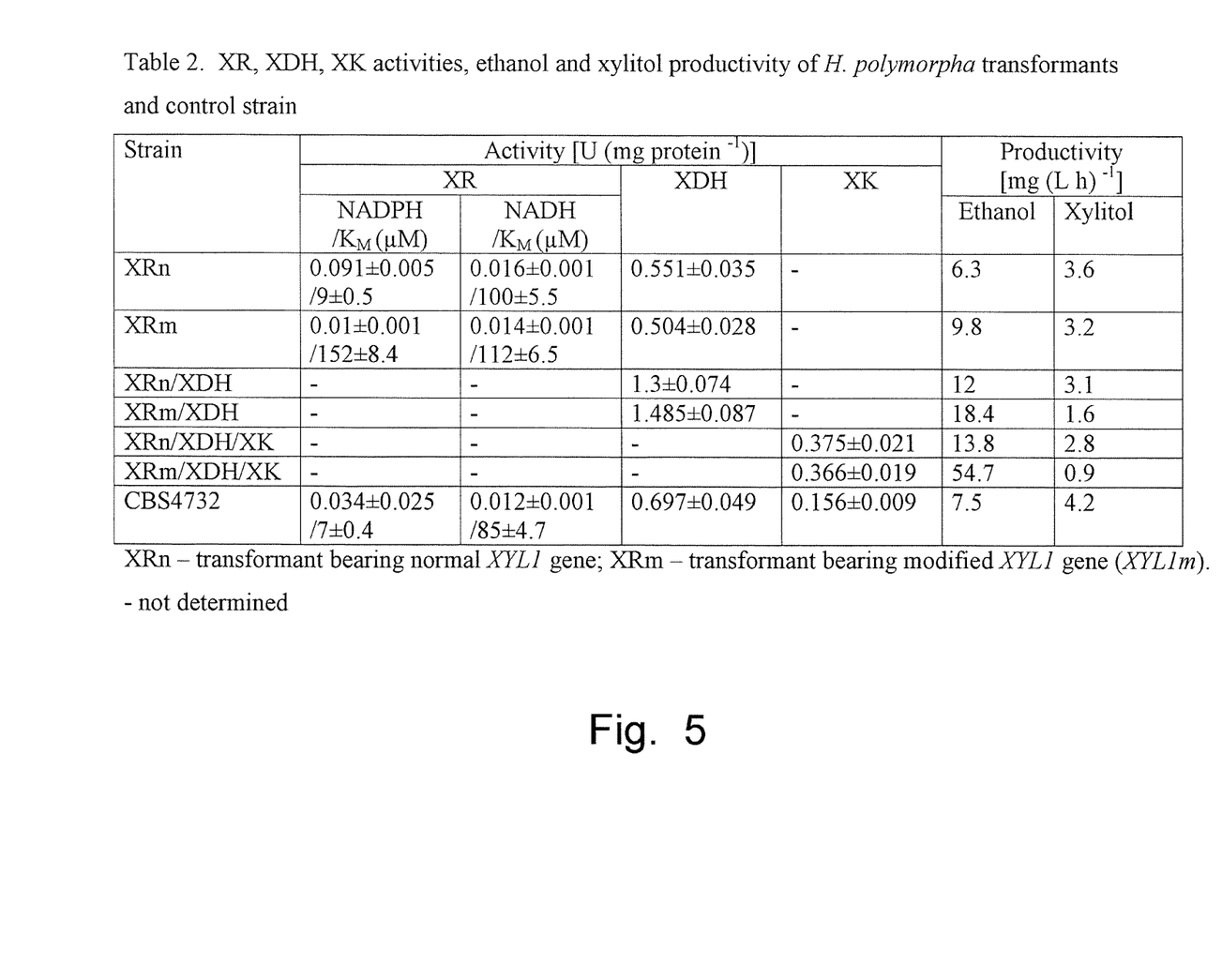
FIG. 5. Table 2 showing XR, XDH, XK activities, as well as the ethanol and xylitol productivity of *H. polymorpha* transformants described herein in comparison to a control strain.
Figure 6A:
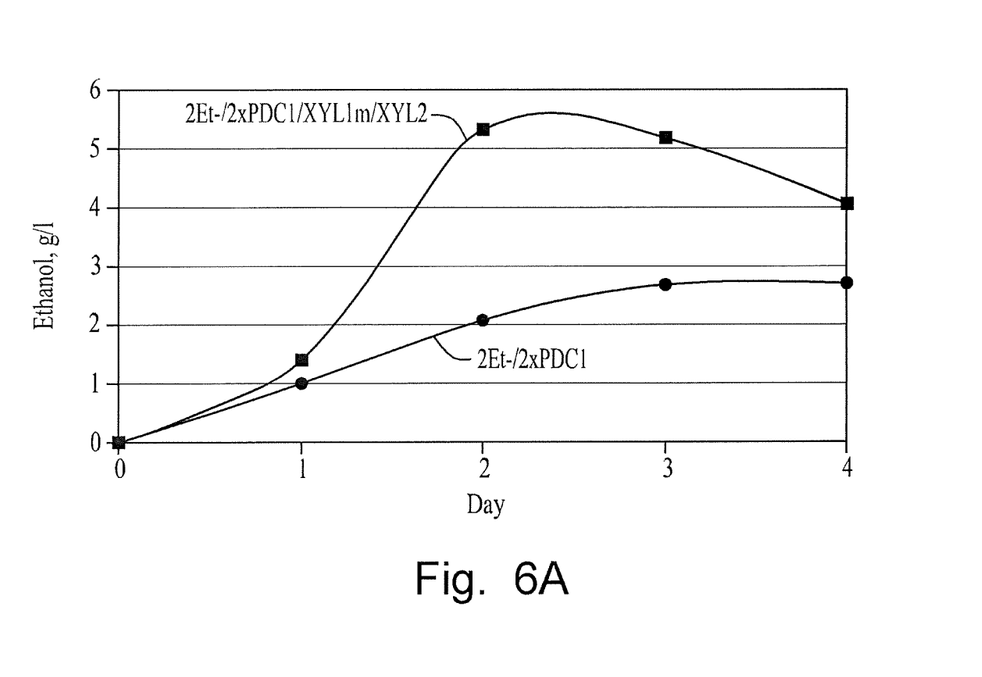
FIG. 6. Table 3 showing a comparison of xylose fermentations at 48° C. by 2Et-/2×PDC1 and 2Et-/2×PDC1/XRm/XDH.
Figure 6B:
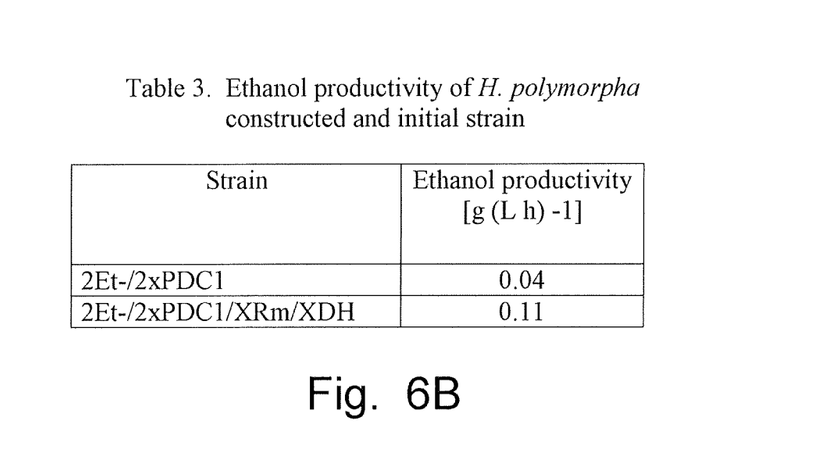

Xylose fermentation by the constructed strain was examined in batch cultures with limited aeration at 48° C. A mineral medium containing xylose (12%) and initial biomass concentration of 2 g (dry weight)×L⁻¹ were used. Results of ethanol production by the constructed strains are shown in Table 3. Ethanol productivity of the 2Et⁻/2×PDC1/XRm/XDH strain was 0.11 g×(L×h)⁻¹, which is 2.7-fold higher than the productivity of the initial strain 2Et⁻/2×PDC. Representative fermentation profiles for the strains 2Et⁻/2×PDC1 and 2Et⁻/2×PDC1/XRm/XDH are shown in FIG. 5.

Overexpression of engineered XR together with native XDH obviously neutralize redox imbalance in constructed recombinant strain of *H. polymorpha*, leading to the significant improvement of ethanol productivity during xylose fermentation.

Discussion

As was described earlier [6], natural xylose-utilizing yeasts display alcoholic fermentation only when their XR possessed NADH-linked activity. The XR of *H. polymorpha* belongs to enzymes with dual cofactor specificity, however NADPH is strongly preferred (>10-fold). In the present case, we focused our efforts on engineering the XR with increased $K_M$ for NADPH. Lysine and asparagine residues were substituted for arginine and aspartic acid, respectively, at the positions 341 and 343 in the frame of cofactor binding site using the site-specific mutagenesis, according to data for the XR gene of *C. tenuis* [33]. The modified version of XR gene under control of the strong constitutive HpGAP promoter was overexpressed on the Δxyl1 background. It resulted in significant increase of $K_M$ for NADPH, while $K_M$ for NADH remained nearly unchanged. Obtained results are in good agreement with reported features of modified XR from *C. tenuis* [33]. The constructed XRm strain showed a slight increase in ethanol productivity as compared to the wild type strain, while the overexpression of native XR had no positive effect. Xylitol production of these strains varied insignificantly. It has to be emphasized that mutated XR reveals significantly lower specific activity with NADPH which resulted in increase of ethanol productivity of the XRm. For further improvement of ethanol production, XDH was expressed together with the modified XR. Overexpression of enzymes for initial two stages of xylose utilization pathway resulted in the 2.4-fold improvement of ethanol productivity accompanied by the 2.6-fold decrease of xylitol production.

In our previous work we developed *H. polymorpha* strains co-overexpressing *E. coli* XI and own XK. The strains were characterized with significant improvement of ethanol production during xylose fermentation [23]. In the present study, the constructed strain XRm/XDH/XK overexpressing the modified XR together with XDH and XK is characterized with significant increase in ethanol productivity (up to 7.4 times) as compared to the wild type strain. Importantly, xylitol production by this strain is reduced considerably: 0.9 mg×(L×h)⁻¹ versus 4.2 mg×(L×h)⁻¹ by the wild type strain. Additional overexpression of XDH and XDH together with XK led to a gradual increase in ethanol productivity and simultaneously a decrease in xylitol production. It may be assumed that the initial stages of xylose utilization are limiting in alcoholic fermentation of xylose in *H. polymorpha*. In FIG. 3, the fermentation profiles of XRm/XDH/XK and XRn/XDH/XK are represented. The consumption of xylose by both constructed *H. polymorpha* strains and the wild type strain during the fermentation was rather low (FIG. 3). This may suggest that xylose uptake in *H. polymorpha* is quite inefficient and corresponding genes coding putative xylose transporters should be cloned and overexpressed. In addition, bottlenecks downstream of XR cannot be excluded and arrant further investigation. The fermentation profile revealed reutilization of synthesized ethanol. The reason of this phenomenon is not understood. In another study the present inventors have isolated a *H. polymorpha* 2EtOH— mutant which is characterized by significant decrease in synthesized ethanol consumption (Ishchuk et al., unpublished). The molecular nature of the corresponding mutation, however, remains unknown.

Recombinant strains of *H. polymorpha* constructed in this study showed significant increase in ethanol productivity during high-temperature xylose fermentation. On the other hand, ethanol production from xylose is still very low as compared to the best current xylose fermenting strains [13a, 17, 34]. Therefore, further efforts have to be applied to improve the xylose alcoholic fermentation in the thermotolerant yeast *H. polymorpha*.

Conclusion

In the present work, co-overexpression of mutated form of XR (K341→R N343→D) together with native XDH and XR in a strain carrying the Δxyl deletion resulted in significant increase (7.4 fold) in ethanol productivity with simultaneous reduction of xylitol production during high-temperature xylose fermentation. The same construction integrated into the chromosome of a *H. polymorpha* strain that a over expresses the *H. polymorpha* pyruvate decarboxylase gene PDC1, but lacking the Δxyl deletion also increases ethanol fermentation from xylose by nearly a factor of three. It is therefore expected that the combination of overexpression of the PDC1 gene and the mutated XR gene in a *H. polymorpha* strain also carrying the Δxyl deletion will enhance ethanol production from xylose even further.

Incorporation by Reference

Each of the following references are cited herein to provide a better understanding of the inventions disclosed herein and to provide descriptions of techniques, sources and materials that will further enable one of ordinary skill in the art to make and use the materials and processes described herein. Accordingly, each of the following references are incorporated herein by reference in their entirety, unless any disclosure provided herein conflicts with the incorporated reference, in which case the conflicting subject matter disclosed herein controls over the cited reference.

Terms in the Claims

In the claims that follow the Reference section hereafter, the term "gene" is a shorthand expression that means any polynucleotide encoding the enzyme identified by the gene named. "Unless expressly stated in the context of the claims," gene" may, but does not necessarily include, non-coding sequences. Unless otherwise stated, the polynucleotide may have the same primary structure as the named gene that is endogenous in the genome of an organism, or be a recombinant form of the named gene linked to other polynucleotide elements, or be a synthetic form of the named gene, or be a mutated form where various elements in the named gene have been changed but the gene still encodes an operable form of the identified enzyme. The term "mutated" means any change in the named gene that makes it different from the endogenous form of the gene. "Native" means the endogenous structure of the gene as it exists in the genome of the organism.

References

1. Zaldivar J, Nielsen J, Olsson L: Fuel ethanol production from lignocellulose: a challenge for metabolic engineering and process integration. *Appl Microbiol Biotechnol* 2001, 56:17-34.
2. Chiang C, Knight S C: Metabolism of D-xylose by molds. *Nature* 1960, 188:79-81.
3. Eliasson A, Christensson C, Wahlbom C F, Hahn-Hagerdal B: Anaerobic xylose fermentation by recombinant *Saccharomyces cerevisiae* carrying XYL1, XYL2, and XKS1 in mineral medium chemostat cultures. *Appl Environ Microbiol* 2000, 66:3381-3386.
4. Tantirungkij M, Nakashima N, Seki T, Yoshida T: Construction of xylose-assimilating *Saccharomyces cerevisiae*. *J Ferment Bioeng* 1993, 75:83-88.
5. Toivari M H, Aristidou A, Ruohonen L, Penttila M: Conversion of xylose to ethanol by recombinant *Saccharomyces cerevisiae*: importance of xylulokinase (XKS1) and oxygen availability. *Metab Eng* 2001, 3:236-249.
6. Bruinenberg P M, de Bot P H M, van Dijken J P, Scheffers W A: NADH-linked aldose reductase: the key to anaerobic fermentation of xylose by yeasts. *Appl Microbiol Biotechnol* 1984, 19:256-260.
7. Bruinenberg P M, Peter H M, van Dijken J P, Scheffers W A: The role of redox balances in the anaerobic fermentation of xylose by yeasts. *Eur J Appl Microb Biotech* 1983, 18:287-292.
8. Kotter P, Ciriacy M: Xylose fermentation by *Saccharomyces cerevisiae*. *Appl Microbiol Biotechnol* 1993, 38:776-783.
9. Walfridsson M, Anderlund M, Bao X, Hahn-Hagerdal B: Expression of different levels of enzymes from the *Pichia stipitis* XYL1 and XYL2 genes in *Saccharomyces cerevisiae* and its effects on product formation during xylose utilisation. *Appl Microbiol Biotechnol* 1997, 48:218-224.
10. Eliasson A, Hofmeyr J H S, Pedler S, Hahn-Hagerdal B: The xylose reductase/xylitol dehydrogenase/xylulokinase ratio affects product formation in recombinant xylose-utilising *Saccharomyces cerevisiae*. *Enzyme Microb Technol* 2001, 29:288-297.
11. Jin Y S, Jeffries T W: Changing flux of xylose metabolites by altering expression of xylose reductase and xylitol dehydrogenase in recombinant *Saccharomyces cerevisiae*. *Appl Biochem Biotechnol* 2003, 105-108:277-286.
12. Karhumaa K, Fromanger R, Hahn-Hagerdal B, Gorwa-Grauslund M F: High activity of xylose reductase and xylitol dehydrogenase improves xylose fermentation by recombinant *Saccharomyces cerevisiae*. *Appl Microbiol Biotechnol* 2007, 73:1039-1046.
13. Jeppsson M, Bengtsson O, Franke K, Lee H, Hahn-Hagerdal B, Gorwa-Grauslund M F: The expression of a *Pichia stipitis* xylose reductase mutant with higher K(M) for NADPH increases ethanol production from xylose in recombinant *Saccharomyces cerevisiae*. *Biotechnol Bioeng* 2006, 93:665-673.
13a. Petschacher B, Nidetzky B. Altering the coenzyme preference of xylose reductase to favor utilization of NADH enhances ethanol yield from xylose in a metabolically engineered strain of *Saccharomyces cerevisiae*. *Microb. Cell Fact.* 2008 7:9 doi:10.1186/1475-2859-7-9.
14. Jeppsson M, Johansson B, Hahn-Hagerdal B, Gorwa-Grauslund M F: Reduced oxidative pentose phosphate pathway flux in recombinant xylose-utilizing *Saccharomyces cerevisiae* strains improves the ethanol yield from xylose. *Appl Environ Microbiol* 2002, 68:1604-1609.
15. Verho R, Londesborough J, Penttila M, Richard P: Engineering redox cofactor regeneration for improved pentose fermentation in *Saccharomyces cerevisiae*. *Appl Environ Microbiol* 2003, 69:5892-5897.
16. Roca C, Nielsen J, Olsson L: Metabolic engineering of ammonium assimilation in xylose-fermenting *Saccharomyces cerevisiae* improves ethanol production. *Appl Environ Microbiol* 2003, 69:4732-4736.
17. van Maris A J A, Winkler A A, Kuyper M., de Laat W T A M, van Dijken J P, Pronk J T Development of Efficient Xylose Fermentation in *Saccharomyces cerevisiae*: Xylose Isomerase as a Key Component. *Adv. Biochem. Engin. Biotechnol.* 2007, 108:79-204.
18. Hahn-Hagerdal B, Wahlbom C F, Gardonyi M, van Zyl W H, Cordero Otero R R, Jonsson L J: Metabolic engineering of *Saccharomyces cerevisiae* for xylose utilization. *Adv Biochem Eng Biotechnol* 2001, 73:53-84.
19. Karhumaa K, Hahn-Hagerdal B, Gorwa-Grauslund M F: Investigation of limiting metabolic steps in the utilization of xylose by recombinant *Saccharomyces cerevisiae* using metabolic engineering. *Yeast* 2005, 22:359-368.
20. Ho N W, Chen Z, Brainard A P: Genetically engineered *Saccharomyces* yeast capable of effective cofermentation of glucose and xylose. *Appl Environ Microbiol* 1998, 64:1852-1859.
21. Ryabova O B, Chmil O M, Sibirny A A: Xylose and cellobiose fermentation to ethanol by the thermotolerant methylotrophic yeast *Hansenula polymorpha*. *FEMS Yeast Res* 2003, 4:157-164.
22. Voronovsky A, Ryabova O, Verba O, Ishchuk O, Dmytruk K, Sibirny A: Expression of xylA genes encoding xylose isomerases from *Escherichia coli* and *Streptomyces coelicolor* in the methylotrophic yeast *Hansenula polymorpha*. *FEMS Yeast Res* 2005, 5:1055-1062.
23. Dmytruk O V, Voronovsky A Y, Abbas C A, Dmytruk K V, Ishchuk O P, Sibirny A A: Overexpression of bacterial xylose isomerase and yeast host xylulokinase improves xylose alcoholic fermentation in the thermotolerant yeast *Hansenula polymorpha*. *FEMS Yeast Res* 2008, 8:165-173.
24. Gellissen G: *Hansenula polymorpha: Biology and Applications*. Weinheim: Wiley-VCH; 2002.

25. Ramezani-Rad M, Hollenberg C P, Lauber J, Wedler H, Griess E, Wagner C, Albermann K, Hani J, Piontek M, Dahlems U, Gellissen G: The *Hansenula polymorpha* (strain CBS4732) genome sequencing and analysis. *FEMS Yeast Res* 2003, 4:207-215.
26. Lahtchev K L, Semenova V D, Tolstorukov I I, van der Klei I, Veenhuis M: Isolation and properties of genetically defined strains of the methylotrophic yeast *Hansenula polymorpha* CBS4732. *Arch Microbiol* 2002, 177:150-158.
27. Sambrook J, Fritsh E F, Maniatis T: *Molecular Cloning: A Laboratory Manual*. New York: Cold Spring Harbor Laboratory, Cold Spring Harbor; 1989.
28. Faber K N, Haima P, Harder W, Veenhuis M, Ab G: Highly-efficient electrotransformation of the yeast *Hansenula polymorpha*. *Curr Genet* 1994, 25:305-310.
29. Sohn J H, Choi E S, Kang H A, Rhee J S, Agaphonov M O, Ter-Avanesyan M D, Rhee S K: A dominant selection system designed for copy-number-controlled gene integration in *Hansenula polymorpha* DL-1. *Appl Microbiol Biotechnol* 1999, 51:800-807.
30. Simpson F J: D-xylulokinase. *Methods in Enzymology* 1966, 9:454-458.
31. Gonchar M V, Maidan M M, Sibirny A A: A new oxidaseperoxidase kit "Alcotest" for ethanol assays in alcoholic beverages. *Food Technol Biotechnol* 2001, 39:37-42.
32. Deschatelets L, Yu E K: A simple pentose assay for biomass conversion studies. *Appl Microbiol Biotechnol* 1986, 24:379-385.
33. Petschacher B, Leitgeb S, Kavanagh K L, Wilson D K, Nidetzky B: The coenzyme specificity of *Candida tenuis* xylose reductase (AKR2B5) explored by site-directed mutagenesis and X-ray crystallography. *Biochem J* 2005, 385:75-83.
34. Kaisa Karhumaa, Rosa Garcia Sanchez, Barbel Hahn-Hagerdal and Marie-F. Gorwa-Grauslund: Comparison of the xylose reductase-xylitol dehydrogenase and the xylose isomerase pathways for xylose fermentation by recombinant *Saccharomyces cerevisiae*. *Microb. Cell Fact.* 2007, 6:5 doi:10.1186/1475-2859-6-5.
35. Ishchuk O P, Voronovsky A Y, Stasyk O V, Gayda G Z, Gonchar M V, Abbas C A, Sibirny A A. Improvement of xylose high-temperature fermentation in *Hansenula polymorpha* due to overexpression of the PDC1 gene coding for pyruvate decarboxylase. *FEMS Yeast Res,* 2008 (in press)
36. Abbas C, Ryabova O, Ishchuk O, Stasyk O, Voronovsky A, Sibirny A. Increased ethanol production from xylose. U.S. Provisional Patent Application No. 60/923,605, 2008.
37. Dmytruk O V, Dmytruk K V, Abbas C A, Voronovsky A Y, Sibirny A A. Engineering of xylose reductase and overexpression of xylitol dehydrogenase and xylulokinase improves xylose alcoholic fermentation in the thermotolerant yeast *Hansenula polymorpha*. *Microbial Cell Factories (in preparation)*.

We claim:

1. A recombinant *Hansenula polymorpha* strain comprising at least one gene encoding a xylitol dehydrogenase enzyme, at least one gene encoding a xylose reductase enzyme, and at least one gene encoding a xylulokinase enzyme, each of said genes being operably linked to at least one promoter that overexpresses said genes in said *H. polymorpha* strain when compared to a corresponding parent *H. polymorpha* strain that is identical but lacking said genes, wherein said recombinant *H. polymorpha* strain produces 4.0 to 7.4 fold more ethanol when fermented in a media containing xylose than the corresponding parent *H. polymorpha* strain not containing said genes, wherein said gene encoding a xylose reductase enzyme encodes a xylose reductase enzyme which comprises all of SEQ ID NO: 4 except for two substitutions at positions 341 and 343, wherein said substitutions are the replacement of a lysine residue at a position corresponding to position 341 of SEQ ID NO: 4 with an arginine and the replacement of an arginine at a position corresponding to position 343 of SEQ ID NO: 4 with an aspartic acid, and wherein said recombinant *Hansenula polymorpha* strain further comprises at least one nucleic acid encoding a pyruvate decarboxylase enzyme endogenous to the parent *H. polymorpha* strain operably linked to a promoter that overexpresses said pyruvate decarboxylase enzyme in the recombinant *H. polymorpha* strain when compared to said parent *H. polymorpha* strain.

2. The recombinant *H. polymorpha* strain of claim 1 wherein each of said genes is integrated into the *H. polymorpha* chromosome.

3. The recombinant *H. polymorpha* strain of claim 1 wherein the *H. polymorpha* strain has a mutation rendering at least one native gene encoding a xylose reductase inoperable.

4. The recombinant *H. polymorpha* strain of claim 1 wherein at least one promoter comprises a glyceraldehyde-phosphate dehydrogenase promoter obtained from *H. polymorpha* (HgGAP).

5. A process for making ethanol comprising growing the recombinant *H. polymorpha* strain of claim 1 in a media comprising xylose under conditions that cause the recombinant *H. polymorpha* to make ethanol.

* * * * *